United States Patent [19]

Vartsky et al.

[11] Patent Number: 4,556,068
[45] Date of Patent: Dec. 3, 1985

[54] IN-VIVO MEASUREMENT OF LITHIUM IN THE BRAIN AND OTHER ORGANS

[75] Inventors: David Vartsky, Yavne, Israel; Lucian Wielopolski, Shirley, N.Y.; Anthony F. LoMonte, Wading River, N.Y.; Kenneth J. Ellis, Bayport, N.Y.; Stanton H. Cohn, Smithtown, N.Y.

[73] Assignee: The United States of America as represented by the Department of Energy, Washington, D.C.

[21] Appl. No.: 526,762

[22] Filed: Aug. 26, 1983

[51] Int. Cl.[4] .............................................. A61K 43/00
[52] U.S. Cl. ..................................... 128/719; 128/659
[58] Field of Search ............... 128/1 R, 653, 654, 659, 128/719; 376/158

[56] References Cited

U.S. PATENT DOCUMENTS

| | | | |
|---|---|---|---|
| 4,202,345 | 5/1980 | Farella et al. | 128/659 X |
| 4,346,583 | 8/1982 | Hoogstraat | 128/719 X |
| 4,404,973 | 9/1983 | Lancaster et al. | 128/659 X |
| 4,425,319 | 1/1984 | Yokoyama et al. | 128/659 X |
| 4,430,320 | 2/1984 | Shigematsu et al. | 128/659 X |
| 4,446,869 | 5/1984 | Knodle | 128/719 X |

Primary Examiner—Edward M. Coven
Attorney, Agent, or Firm—Vale P. Myles; James W. Weinberger; Judson R. Hightower

[57] ABSTRACT

The lithium used clinically and distributed in organs such as the brain or kidney of humans and other exhaling animals is determined in-vivo by means of neutron radiation and measuring in the exhaled air elemental tritiated hydrogen released from the tritium reaction by the reaction $^6Li(n,\alpha)T$. The tritium atoms so released are transformed in part in the surrounding aqueous solution to form gaseous tritiated hydrogen which has a small solubility in body tissues and liquids and thus appears quickly in the breath. After a recipient fasts and is irradiated with neutrons, the air exhaled in the breath for a given time after irradiation is captured and processed to remove water, isolate hydrogen and measure the tritiated hydrogen with a gaseous organ-methane counter.

12 Claims, 3 Drawing Figures

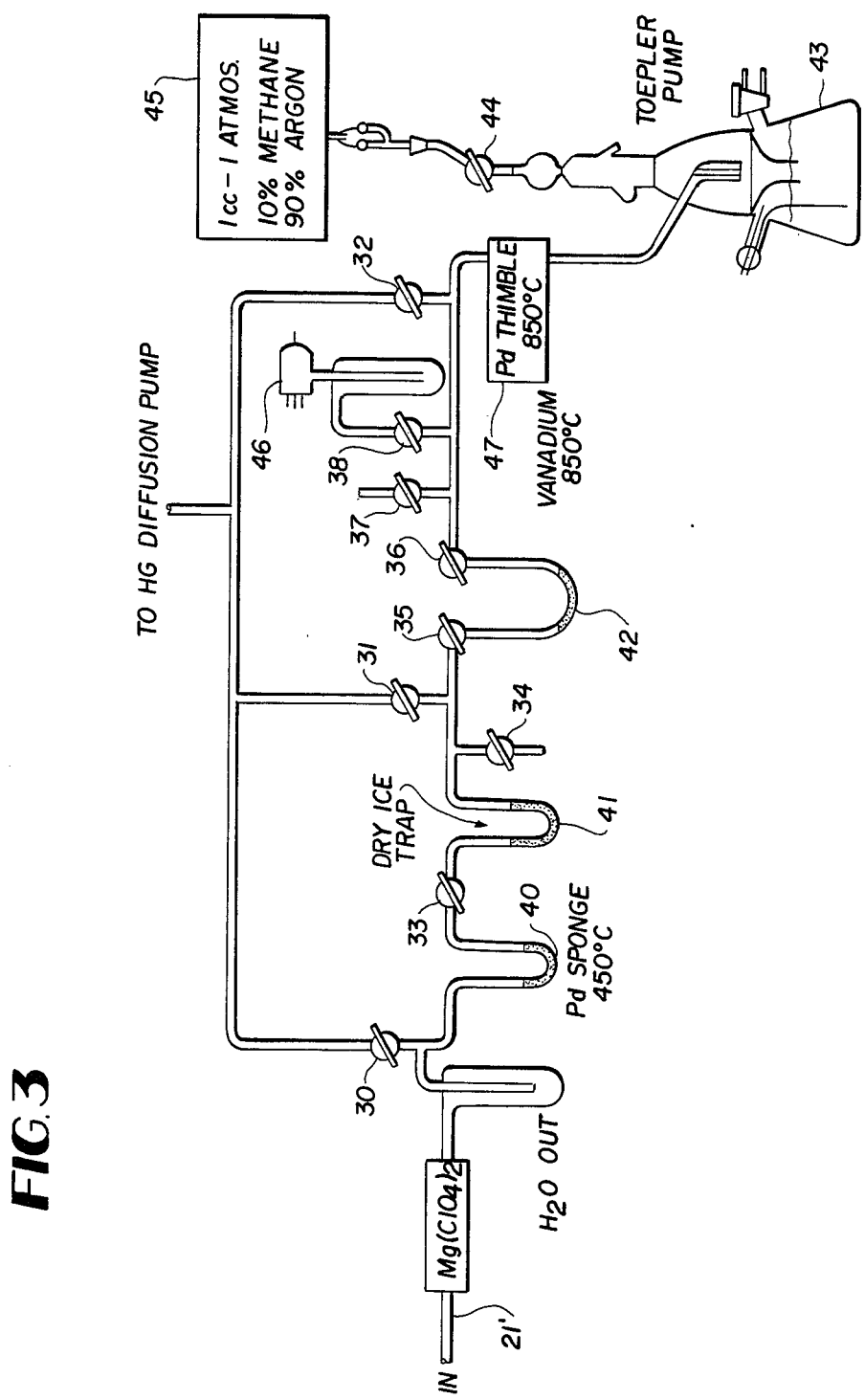

IN-VIVO MEASUREMENT OF LITHIUM IN THE BRAIN AND OTHER ORGANS

DISCLOSURE OF THE INVENTION

The invention described herein was made or conceived in the course of, or under a contract with, the United States Department of Energy.

The United States Government has rights in this invention pursuant to Contract Number DE-AC02-76CH00016, between the United States Department of Energy and Associated Universities, Inc.

This invention relates to detection of lithium and more particularly it relates to the in-vivo detection of clinically aministered lithium salts resident in organs such as the brain and kidney.

BACKGROUND ART

Heretofore the detection of lithium in animal organs has been achieved only by post mortem specimens preferred in-vivo. This type of study of lithium level in different tissues and particularly in the brain is reported in 1976 by M. A. Spirites in "Pharmaceutical Biochemistry and Behavior", Volume 5, pages 143 to 147 and in 1980 by M. Thellier et al., in "Nature", Volume 283, pages 299 to 302. In view of use of lithium clinically for the treatment of mania and its effect on attenuation of manic and depressive episodes, it is important to be able to measure in-vivo the amount of lithium in body tissues and organs (in particular the brain and kidney).

Because of long term clinical administration of lithium salts and side effects, it is essential to monitor the action on the brain and any possible kidney overload or damage.

In connection with in-vivo measurements of humans there are many problems to be resolved to find a method that is acceptable as a procedural measure, particularly in view of low concentrations of lithium in the form of lithium salts resident in the body, the sensitiveness of the brain area, the inability to take specimens, etc. Also the accuracy of measurement of small concentrations of the lithium without serious interruption of life processes and thus necessarily by indirect methods presents another set of problems. Furthermore, the time it takes to ascertain the measurements is critical, in order to make them relate to the clinical effects and to investigate adequacy of doses, etc.

Thus, the objectives of this invention are to resolve the foregoing problems and to provide an in-vivo measurement of lithium concentrations in particularly the human body with enough accuracy to advance the clinical and therapeutic usage thereof.

The determination of lithium in various materials by the neutron activation method using the $^6Li(n,\alpha)T$ reaction has been reported by B. P. Zverev et al., in Soviet Atomic Energy (U.S.A.), Vol. 32, No. 1, Jan. 1972, pp. 35-37. H. I. Kallmann et al., 2,288,717 —July 7, 1942 also teaches liberation of tritium from lithium isotopes by neutron irradiation for forming images to thus show the nature of the neutron beam irradiation pattern.

However, there is no known method of in-vivo determination of lithium present in animal tissues and organs prior to this invention.

DISCLOSURE OF THE INVENTION

We have discovered an in-vivo method of measurement of the amount of lithium present in tissue and organs of breathing animals. Apparatus and techniques developed in the lithium measurements permit accurate diagnosis of the lithium present in the brain, kidneys, or body tissues. It is not known how lithium is distributed between plasma and tissues, etc.

Therapeutic use of lithium salts for manic depression has been known for about twenty years, but the mechanism of action is not yet known. In view of the importance of the clinical use of lithium, it is desirable to study its distribution and dynamics in-vivo and particularly the concentrations of lithium in the brain and kidneys in a method compatible with human use, where only post mortem analysis from specimens previously has been available. Lithium could not be studied in the conventional manner of other therapeutic drugs or tracers because it does not have a detectable radioactive isotope. Measurements are further complicated by the very small trace amounts present in human, animal and plant tissue. The concentration in human tissue is in the 0.01 $\mu$g/g range, being largest in the cortical bone—0.12 $\mu$g/g.

In this invention the lithium-neutron interaction—$^6Li(n,\alpha)T$—is used with the 7.4% $^6Li$ isotope. Thus, the lithium is irradiated with thermal neutrons originating from 4.8 MeV neutrons to produce tritium atoms. In the aqueous in-vivo environment the tritium atoms react with water to form HT gas and HTO in the ratio of 0.60 (T. Kambara et al., "Journal of Inorganic Nuclear Chemistry", Vol. 21, pages 210 to 215, 1961). The HTO created in the body mixes with body fluids and our calculations show that this dilution of tritium obscures the readings in the natural tritium background content of water. However, the HT is quite inert and has small solubility in body tissues and liquids.

HT gas created in the tissue by the neutron irradiation of the lithium salts diffuses from the tissue to the blood and is transported to the lungs where it is brought into equilibrium with the alveolar gas. Hydrogen diffuses rapidly in tissues. Because of its low water to gas partition coefficient, the pulmonary circulation rapidly removes it from arterial blood. Thus, in less than 25 minutes following irradiation, 99% of the tritium produced will be exhaled.

A minute amount of hydrogen gas and less tritium present in the breath is diluted by several hundreds of liters of air. Also hydrogen gas is present in air and is manufactured by human intestinal organisms. Tritium background levels are present in the environment. Thus, to make feasible accurate measurements of minute traces of tritium which identify the amount of lithium present, various background diluents need be eliminated, neutralized or otherwise handled in a critical procedure that makes possible a quantitative analysis or survey of the presence of tritium. The tritium in the atmosphere, which provides a significant background interference, is removed by excluding hydrogen from the air inhaled by the patient under study. Also the patient is required to fast for at least 12 hours before measurement to remove the source of intestinally produced hydrogen by fermentation of poorly digested food.

To remove diluents and to process the exhaled air for establishing the tritium level due to irradiation of lithium salts, water is removed from the moist breath, and air is accumulated over a designated period following irradiation. Then hydrogen is removed from the air to concentrate the tritium tracer element, and the tritium is electronically counted quantitatively and converted to indicate the lithium concentration in the irradiation zone. Irradiation is confined for example to the brain, the kidney, etc.

BRIEF DESCRIPTION OF THE DRAWINGS

In the following:

FIG. 3 is a sketch of the tritium isolation and counting portion of the system which treats the exhaled air of a patient under test.

THE PREFERRED EMBODIMENT

Natural lithium consists of two isotopes, 92.6% $^7Li$ and 7.4% $^6Li$. The $^6Li(n,\alpha)T$ reaction with thermal neutrons liberates energy of 4.8 MeV in the form of kinetic energies of the $\alpha$ and T particles. The recoiling tritium atom (T) in an aqueous environment reacts with water to form HT gas and HTO liquid by hydrogen abstraction and isotopic exchange respectively. The HT/HTO ratio remains substantially fixed for a wide range of conditions such as pH.

As the HTO created in the body following irradiation of the lithium present by neutrons mixes with body fluids, other sources of tritium present which dilute and mask its presence due to lithium. Calculations show that the measurement of HTO is thus impractical. However, the HT gas created in the tissue diffuses to the blood and is transported to the lungs where it is brought into equilibrium with the alveolar gas. Hydrogen diffuses rapidly in tissues. With its low water to gas partition coefficient the pulmonary circulation removes it rapidly from the blood. Thus in about 25 minutes following irradiation, 99% of the tritium gas produced will be exhaled.

To afford quantitative measurement, the minute amount of hydrogen gas present in the breath is concentrated by separating it from the several hundreds of liters of air. Then the tritium activity can be measured by well known counting techniques.

In order to quantitatively measure trace amounts of lithium with relatively small tritium counts, it is important to reduce any potential errors from background tritium that may interfere with the measurement. The two main background sources are (1) the tritium level present in the atmosphere, a concentration of $10^4$ to $10^6$ tritium units which would give 420 to 1250 counts per day and (2) intestinal hydrogen produced from poorly digested fermentable materials by bacterial action with an elevated breath hydrogen of the order of 50 parts per million having tritium concentration of $10^3$ to $10^4$ tritium units with a corresponding count of five to 150 counts per day. The tritium in the atmosphere is accordingly removed from air inhaled by the patient under test. The intestinal hydrogen is removed by requiring the patient to fast for at least 12 hours before irradiation.

Figure 1:
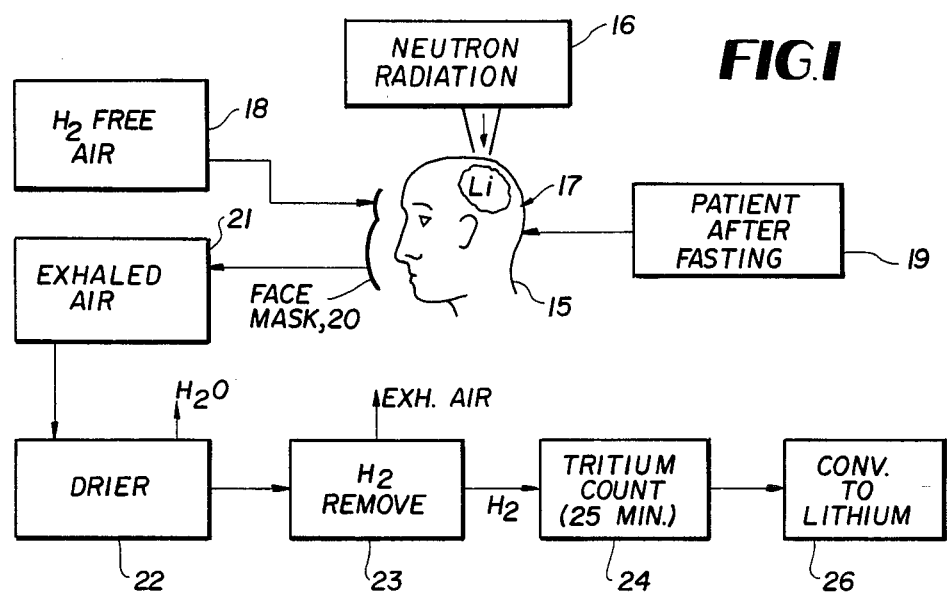
FIG. 1 is a block diagram sketch of the system for detecting lithium in-vivo in organs or tissue embodying the invention.

Therefore the block diagram system representation of FIG. 1 represents the method afforded by this invention for quantitatively in-vivo measuring the presence of lithium in a limited area of the animal tissue or organ system, typically the brain or kidney.

The live human or other animal patient 15, having been clinically treated with lithium salts is subjected to neutron irradiation 16 of a limited organ or tissue area under investigation such as the brain 17. Background noise due to free tritium in the air is eliminated by providing $H_2$ free air 18 for the patient 15 to inhale. Also as indicated at 19, the patient has fasted to eliminate background noise due to intestinally generated $H_2$. A human patient may wear a facemask 20 for the breathing of $H_2$ free air and the exhaling of air 21 into the breath processing system.

In processing the exhaled humid breath air, the water is first removed in drier 22. Then the $H_2$, which represents and contains the tritiated hydrogen (T) released by the irradiation of the lithium salts present in the irradiated zone, is isolated from the exhaust air at 23. Tritium is counted by a state of the art tritium counter 24 available for atomic energy measurements for the quantity of air exhaled during the 25 minutes following irradiation to capture all of the tritium produced by the reaction $^6Li(n,\alpha)T$ in the patient 15. By appropriate normalization and calculation, the tritium count is converted at 26 to a quantitative measurement of the lithium present (in the brain, kidney or the like).

Figure 2:
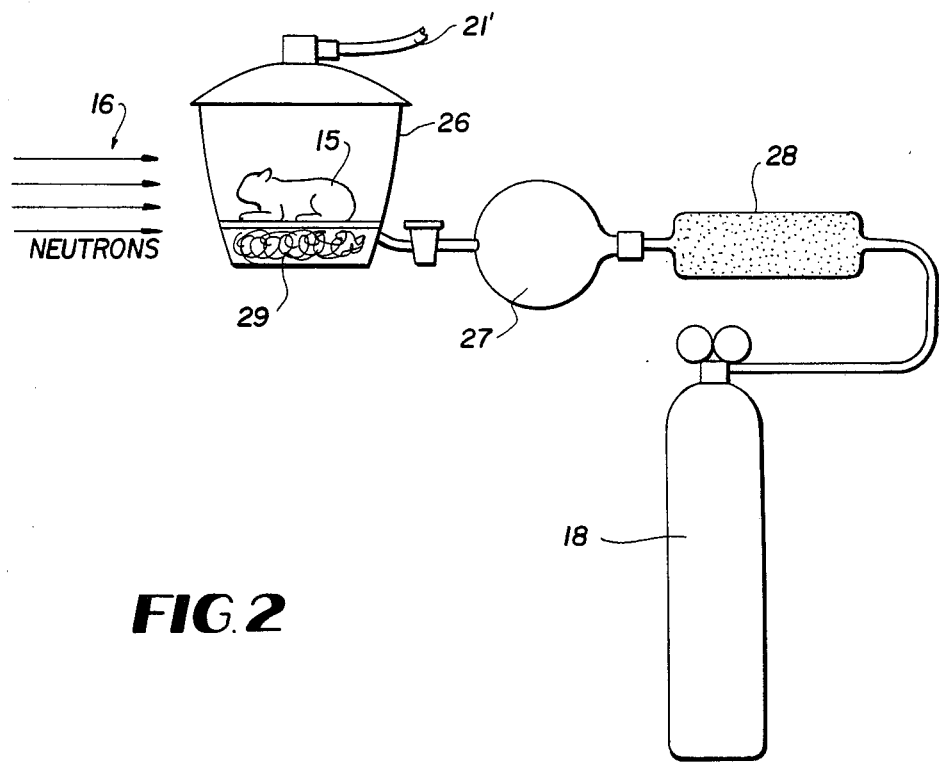
FIG. 2 is a partial system sketch showing the removal of hydrogen from inhaled air as a background source of tritium.

As shown in FIG. 2, where the patient 15 is a guinea pig, a closed environment housing chamber 26, transparent to the neutron irradiation 16 is used to confine the exhaled air delivered at tubing 21'. Preferably the $CO_2$ is removed by an absorber 29. The balloon 27 is a breathing bag maintaining a constant pressure within the chamber 26. Hydrogen is removed from the inhaled air by the palladium coated silicon gel cartridge 28 through which the breathing air from cylinder 18 is passed.

As shown in FIG. 3, the exhaled air is dried by a $Mg(ClO_4)_2$ cartridge 22. Removal of water and exhaust air, etc. is achieved by operation of valves 30, 31, 32 to the mercury diffusion exhaust pump, and various segments of the exhaled air processing system can be isolated by valves 33 to 38, etc. Thus, the various method steps are operated in a desired sequence.

After water is removed at cartridge 21, the dried exhaled air is passed through hot palladium sponge 40 to convert hydrogen to water and trap the water in a dry ice trap 41. Then with valves 30, 33, 35 and 32 closed, the exhaled air can be exhausted to the diffusion pump.

Hot vanadium in furnace 42 is cooled to room temperature to absorb hydrogen from the trap 41 forming $VH_2$ (with valves 33, 31, 36 closed and valve 35 open). After this, valve 31 is open and other gas residues are exhausted by the diffusion pump.

Afte this, the vanadium furnace 42 is reheated to release the hydrogen with valves 32, 35 closed and valve 36 open to pass the hydrogen for measurement in the Toepler pump 43. Valve 44 is closed for measurement, and openend for a tritium count in the counter 45 which is designed for low level tritium counting with about one cc of 10% methane 90% argon at one atmosphere.

Provisions for evacuation by other vacuum or pump systems are made through valves 34 and 37. A blower system 46 is used in connection with valve 38 as required. Also the $H_2$ is purified by means of palladium thimble 47 at 850° C. in the inlet to the Toepler pump 43 if desired.

Care is used in the counter 45 which is constructed of fused silica low in $^{40}K$ and with cathode made out of purified copper in which the solubility of hydrogen is low. All materials which could absorb hydrogen are eliminated.

EXAMPLE 1

A carefully measured volume of hydrogen mixed with a large quantity of air is passed through the system. $H_2$ recovery in six runs as measured by the Toepler pump was 99±2%.

EXAMPLE 2

The background tritium count of the counter 45 to atmospheric air was 13±3 counts per day.

EXAMPLE 3

When using the disclosed system, a patient treated with a neutron dose of 1 rem to the brain containing approximately 1 mg of Li provides a tritium activity level count of about 70 c/day from exhaled breath.

When the $^6Li$ isotope is used as a drug, the activity is increased to a level of 900 c/day.

EXAMPLE 4

A fasting (for 24 hours) patient untreated by lithium and radiation exhaled 30 liters of air passed through the system. The volume of hydrogen was 0.189 cc or 6.3 ppm by volume. The tritium activity level was 97±10 counts/day due to atmospheric air inhaled by the patient and intestinally generated $H_2$.

EXAMPLE 5

In the absence of fasting the level of activity in the patient in Example 4 was increased by about 50 ppm of hydrogen.

EXAMPLE 6

A control guinea pig untreated with $^6Li$ produced an activity level for tritium of 328 c/day.

EXAMPLE 7

Exhalation time on a $^6Li$ treated guinea pig irradiated over the whole body showed a half-life of about fifteen minutes. The half-life was shorter with only the brain zone irradiated.

It is therefore evident from the foregoing disclosure that this invention has advanced the state of the art by providing an in-vivo method of quantitative measurement of lithium present in selected patient's organs or body tissue subjected to neutron irradiation. Those features of novelty defined with particularity in the claims are believed representative of the spirit and nature of the invention.

We claim:

1. An in-vivo method of measuring the amount of lithium present in tissue and organs of a beathing mammal, comprising the steps of:
    (a) irradiating with neutrons a selected area of the lithium containing body of said mammal, thereby to produce tritium atoms in the body, by the nuclear reaction $^6Li(n,\alpha)T$ taking place, and to effect the production of elemental tritiated hydrogen (HT) gas within said body, as a reaction product of the tritium atoms with water present in the body;
    (b) capturing air exhaled from said body during a designated time period following the neutron irradiation of said area;
    (c) measuring the amount of HT gas in the captured air;
    (d) normalizing the measurement of captured HT gas, and performing calculations to convert said measurement to a corresponding quantitive measurement of $L_i$, thereby to determine the amount of $L_i$ present in said selected area of the body.

2. The method defined in claim 1 wherein the measuring step (c) comprises the ordered steps of extracting hydrogen gas from the exhaled air, and measuring the tritiated hydrogen present in the extracted hydrogen gas.

3. The method defined in claim 2 comprising the step of measuring the tritiated hydrogen with 10% methane and 90% argon counting gas mixture at about one atmosphere.

4. The method defined in claim 2 including the step of reducing the tritiated hydrogen background presence in the exhaled air, from sources other than lithium in the body, before measurement of the tritiated hydrogen.

5. The method defined in claim 14 including in step (b) thereof the steps of passing the exhaled air through a hot palladium sponge to form water from the hydrogen in the air, trapping said water in a dry ice trap, exhausting the residual air, exposing the water to hot vanadium in a vanadium furnace and cooling the resultant vapor to room temperature to form $VH_2$, evacuating the furnace to remove any residual gases, heating the $VH_2$ in the furnace to release $H_2$ and HT, and, according to step (c) of said method, measuring the tritiated hydrogen present in the released $H_2$ and HT, as a measurement proportional to the lithium present in the selected body area.

6. The method defined in claim 5 including, in step (c) thereof, the step of detecting the presence of tritiated hydrogen in a gaseous counter that is provided for that purpose and contains about 1 cc counting gas of 90% argon and 10% methane with a body of used silica that is low in 40 K potassium and a copper cathode to keep solubility of hydrogen low.

7. The method defined in claim 5 including, in step (b) thereof, the step of drying the exhaled air before passing it to said sponge by passing the air successively through a $Mg(ClO_4)_2$ containing cylinder.

8. The method defined in claim 5 including, in step (b) thereof, the step of purifying the released $H_2$ and HT by passing it, through a palladium thimble heated to about 850° C.

9. The method of claim 1 including the preliminary step of fasting the patient for at least 12 hours before performing steps a–d of the method.

10. The method of claim 1, wherein the performance of step b includes capturing said air for about 25 minutes following the irradiation of step (a).

11. The method of claim 1 including in step (a) thereof the step of confining a dose of said radiation to the brain organ of said mammal.

12. The method of claim 11 including, in step (a) thereof, the step of producing a measured irradiation dose of about 1 rem in said brain organ.

* * * * *